United States Patent
Du et al.

(10) Patent No.: US 9,404,516 B1
(45) Date of Patent: Aug. 2, 2016

(54) SYSTEM FOR ESTIMATING A SENSOR OUTPUT

(71) Applicant: Caterpillar Inc., Peoria, IL (US)

(72) Inventors: Hongliu Du, Peoria, IL (US);
Aleksandar Egelja, Peoria, IL (US);
Santosh Ancha, Peoria, IL (US)

(73) Assignee: Caterpillar Inc., Peoria, IL (US)

( * ) Notice: Subject to any disclaimer, the term of this patent is extended or adjusted under 35 U.S.C. 154(b) by 20 days.

(21) Appl. No.: 14/599,238

(22) Filed: Jan. 16, 2015

(51) Int. Cl.
| | | |
|---|---|---|
| *G01N 3/00* | (2006.01) | |
| *F15B 19/00* | (2006.01) | |
| *F15B 15/20* | (2006.01) | |
| *E02F 9/22* | (2006.01) | |
| *G01M 15/05* | (2006.01) | |
| *G01N 30/32* | (2006.01) | |

(52) U.S. Cl.
CPC ............. *F15B 19/005* (2013.01); *E02F 9/2278* (2013.01); *F15B 15/20* (2013.01); *G01M 15/05* (2013.01); *G01N 2030/326* (2013.01)

(58) Field of Classification Search
CPC ...... G01M 15/05; F15B 19/005; F15B 15/20; G01N 2030/326
USPC .................................................. 73/798, 168
See application file for complete search history.

(56) References Cited

U.S. PATENT DOCUMENTS

| | | | |
|---|---|---|---|
| 5,267,441 A | 12/1993 | Devier et al. | |
| 5,720,598 A * | 2/1998 | de Chizzelle | F04B 51/00 417/53 |
| 5,944,492 A | 8/1999 | Konishi et al. | |
| 6,375,433 B1 | 4/2002 | Du et al. | |
| 6,623,247 B2 | 9/2003 | Du | |
| 6,848,254 B2 | 2/2005 | Du | |
| 7,043,975 B2 | 5/2006 | Du | |
| 7,110,924 B2 | 9/2006 | Prewett et al. | |
| 7,130,721 B2 | 10/2006 | Wear et al. | |
| 8,162,618 B2 | 4/2012 | Nakamura et al. | |
| 8,548,661 B2 | 10/2013 | Wu | |
| 8,635,941 B2 | 1/2014 | Du | |
| 8,838,314 B2 | 9/2014 | Bissontz | |
| 2002/0096060 A1* | 7/2002 | Kohno | B30B 1/186 100/35 |
| 2006/0004509 A1* | 1/2006 | Teslak | B60K 6/12 701/84 |
| 2006/0018765 A1* | 1/2006 | Fransson | E02F 9/2217 417/213 |
| 2009/0126361 A1* | 5/2009 | Kakizawa | E02F 9/2235 60/445 |
| 2010/0186401 A1* | 7/2010 | Kauss | F15B 11/003 60/327 |
| 2012/0263604 A1 | 10/2012 | Jung | |
| 2013/0061588 A1* | 3/2013 | Jagoda | B60K 6/12 60/414 |
| 2013/0230413 A1 | 9/2013 | Yamaji | |
| 2014/0023523 A1 | 1/2014 | Berg | |

OTHER PUBLICATIONS

U.S. Appl. No. 14/599,220, filed Jan. 16, 2015.

* cited by examiner

*Primary Examiner* — Max Noori
(74) *Attorney, Agent, or Firm* — Leydig, Voit & Mayer, Ltd.

(57) ABSTRACT

A system for determining an estimated output from a variable displacement hydraulic pump includes a prime mover, and torque, pressure, and displacement sensors. A controller determines the output torque from the prime mover, determines an input torque to the variable displacement hydraulic pump based upon the output torque, determines an output from one of the pressure sensor and the displacement sensor, and determines an inertia torque loss based upon the angular acceleration of the prime mover. The controller further determines a failure of another of the pressure sensor and the displacement sensor and determines an estimated output from the another of the pressure sensor and the displacement sensor based upon the input torque to the variable displacement hydraulic pump, the output from the one of the pressure sensor and the displacement sensor, and the inertia torque loss.

20 Claims, 7 Drawing Sheets

SYSTEM FOR ESTIMATING A SENSOR OUTPUT

TECHNICAL FIELD

This disclosure relates generally to a system for estimating a sensor output and, more particularly, to a system for determining an estimation of an output of a sensor associated with a variable displacement hydraulic pump.

BACKGROUND

Many different types of machines utilize hydraulic systems to operate work implements and hydrostatic drives. Examples of these machines include excavators, backhoes, loaders, haul trucks, and various other machines. The machines typically include a plurality of sensors and use closed-loop feedback systems to monitor the operation of the various systems within the machine.

Due to the complexity and size of the machines and to prevent undesired or uncontrolled operation, the systems are often configured to shut down or substantially reduce the performance of the machine upon the failure of a pressure or displacement sensor. In such case, productivity is lost while waiting for replacement of the inoperative sensor.

U.S. Pat. No. 8,548,661 discloses a hybrid hydraulic excavator having an engine with both a variable displacement hydraulic pump and a motor generator connected to the engine. A controller is operative to determine a calculation value of the hydraulic pump based upon a pump current supplied to the pump and a discharge pressure of the pump using an algorithm, and corrects a hydraulic pump characteristic parameter used in the algorithm based upon an assumed pressure error. The controller further calculates an assumed hydraulic pressure correction output using the corrected hydraulic pump characteristic parameter, and controls the operation of the motor generator based upon the assumed hydraulic pressure correction output.

The foregoing background discussion is intended solely to aid the reader. It is not intended to limit the innovations described herein, nor to limit or expand the prior art discussed. Thus, the foregoing discussion should not be taken to indicate that any particular element of a prior system is unsuitable for use with the innovations described herein, nor is it intended to indicate that any element is essential in implementing the innovations described herein. The implementations and application of the innovations described herein are defined by the appended claims.

SUMMARY

In one aspect, a system for determining an estimated output from a variable displacement hydraulic pump includes a prime mover operatively connected to drive the variable displacement hydraulic pump, a torque sensor for generating torque signals indicative of an output torque from the prime mover, a pressure sensor for generating pressure signals indicative of an output pressure from the variable displacement hydraulic pump, and a displacement sensor for generating displacement signals indicative of a displacement of the variable displacement hydraulic pump. A prime mover speed sensor is operatively associated with the prime mover and is operative to determine an angular acceleration of the prime mover. A controller is configured to receive torque signals from the torque sensor, determine the output torque from the prime mover, determine an input torque to the variable displacement hydraulic pump based upon the output torque, and receive signals from one of the pressure sensor and the displacement sensor. The controller is further configured to determine an output from the one of the pressure sensor and the displacement sensor based upon the signals, determine an inertia torque loss based upon the angular acceleration of the prime mover. The controller is also configured to determine a failure of another of the pressure sensor and the displacement sensor and determine an estimated output from the another of the pressure sensor and the displacement sensor based upon the input torque to the variable displacement hydraulic pump, the output from the one of the pressure sensor and the displacement sensor, and the inertia torque loss.

In another aspect, a controller-implemented method of determining an estimated output from a variable displacement hydraulic pump includes providing a variable displacement hydraulic pump, providing a pressure sensor for generating pressure signals indicative of an output pressure from the variable displacement hydraulic pump, and providing a displacement sensor for generating displacement signals indicative of a displacement of the variable displacement hydraulic pump. The method further includes receiving torque signals from a torque sensor indicative of an output torque from a prime mover, determining the output torque from the prime mover based upon the torque signals, determining an input torque to the variable displacement hydraulic pump based upon the output torque, and receiving signals from one of the pressure sensor and the displacement sensor. The method also includes determining an output from the one of the pressure sensor and the displacement sensor based upon the signals, determining an inertia torque loss based upon an angular acceleration of the prime mover, determining a failure of another of the pressure sensor and the displacement sensor, and determining an estimated output from the another of the pressure sensor and the displacement sensor based upon the input torque to the variable displacement hydraulic pump, the output from the one of the pressure sensor and the displacement sensor, and the inertia torque loss.

In still another aspect, a machine includes a variable displacement hydraulic pump, a prime mover operatively connected to drive the variable displacement hydraulic pump, a torque sensor for generating torque signals indicative of an output torque from the prime mover, a pressure sensor for generating pressure signals indicative of an output pressure from the variable displacement hydraulic pump, and a displacement sensor for generating displacement signals indicative of a displacement of the variable displacement hydraulic pump. A prime mover speed sensor is operatively associated with the prime mover and is operative to determine an angular acceleration of the prime mover. A controller is configured to receive torque signals from the torque sensor, determine the output torque from the prime mover, determine an input torque to the variable displacement hydraulic pump based upon the output torque, and receive signals from one of the pressure sensor and the displacement sensor. The controller is further configured to determine an output from the one of the pressure sensor and the displacement sensor based upon the signals, determine an inertia torque loss based upon the angular acceleration of the prime mover. The controller is also configured to determine a failure of another of the pressure sensor and the displacement sensor, and determine an estimated output from the another of the pressure sensor and the displacement sensor based upon the input torque to the variable displacement hydraulic pump, the output from the one of the pressure sensor and the displacement sensor, and the inertia torque loss.

DETAILED DESCRIPTION

Figure 1:
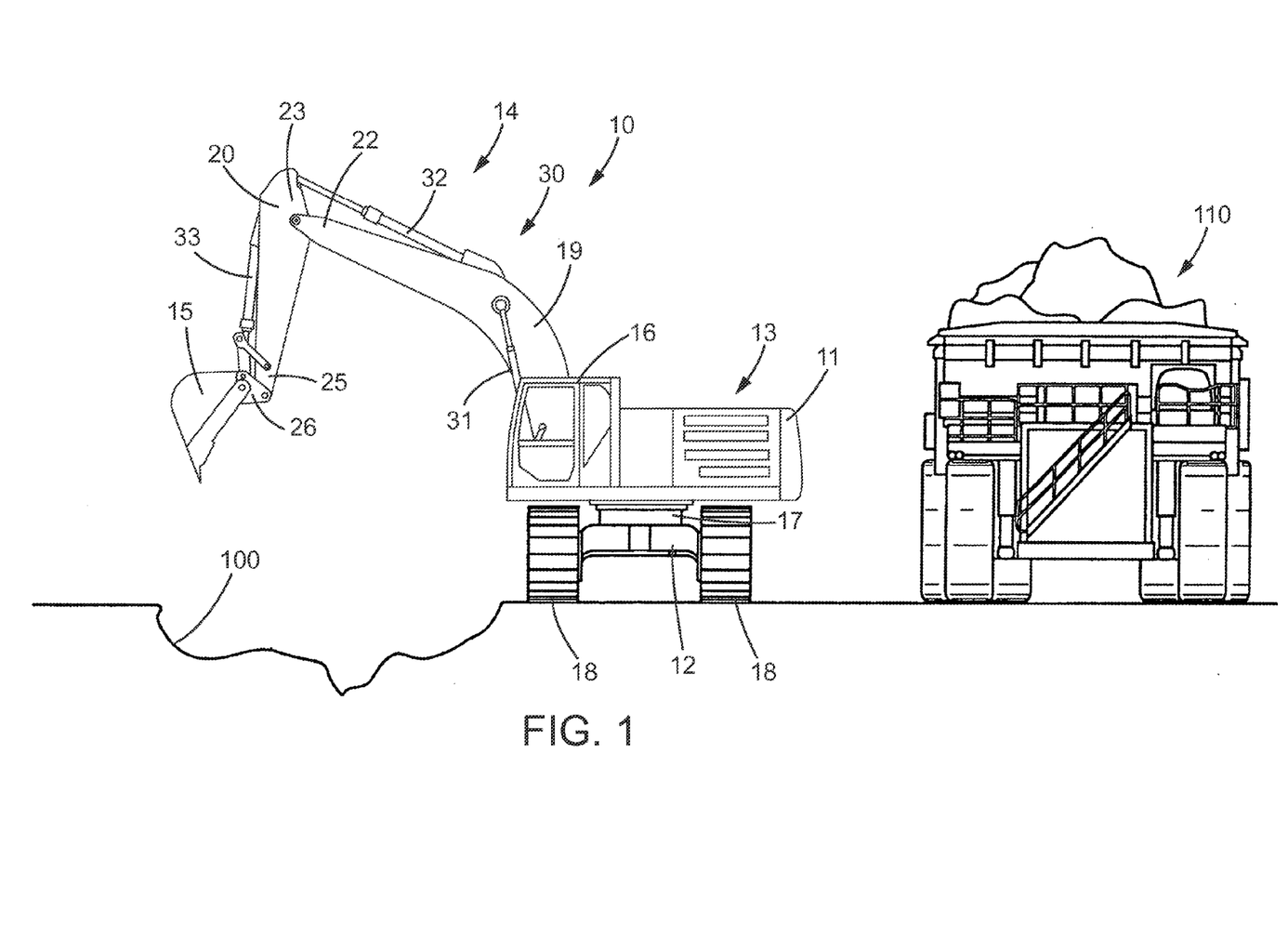
FIG. 1 illustrates a side view of a hydraulic excavator including a sensor output estimation system in accordance with the disclosure and with an adjacent target vehicle.

FIG. 1 illustrates an exemplary machine 10 such as an excavator having multiple systems and components that cooperate to perform an operation such as excavating earthen material from a dig site 100 and loading it onto a nearby target such as haul machine 110. Machine 10 may include a swing member or platform 11, an undercarriage 12, a prime mover 13, and an implement system 14 including a work implement or tool 15 such as a bucket. Other types of work implements may also be used.

Figure 3:
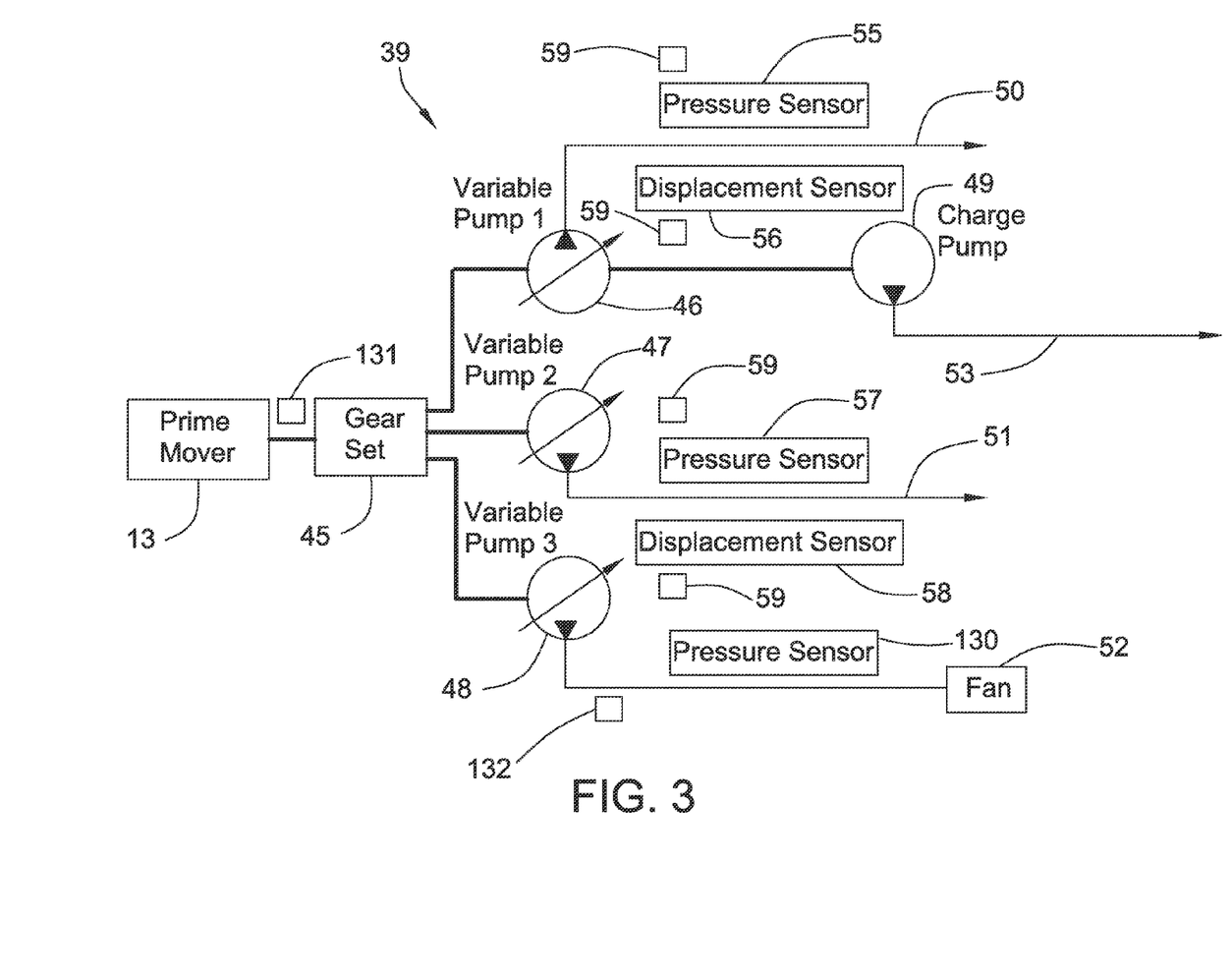
FIG. 3 illustrates a simplified schematic view of a hydraulic power system of the hydraulic excavator of FIG. 1.

Platform 11 may be rotatably disposed on undercarriage 12 and includes an operator station 16 from which an operator may control the operation of machine 10. Rotation of platform 11 relative to undercarriage 12 may be effected by a swing motor 17 (FIG. 3).

Undercarriage 12 may be a structural support for one or more ground-engaging traction devices. The ground engaging traction devices may include one or more tracks 18 configured to allow translational motion of machine 10 across a work surface. Alternatively, the ground engaging fraction devices may include wheels, belts, or other traction devices known in the art.

A prime mover 13 may provide power for the operation of machine 10. Prime mover 13 may embody a combustion engine, such as a diesel engine, a gasoline engine, a gaseous fuel powered engine (e.g., a natural gas engine), or any other type of combustion engine known in the art. Prime mover 13 may alternatively embody a non-combustion source of power, such as a fuel cell or a power storage device such as a battery coupled to a motor. Further, if desired, both a combustion engine and a non-combustion source of power may be provided as a hybrid source of power that operates to increase the efficiency of the machine operation. Prime mover 13 may provide a rotational output to tracks 18, thereby propelling machine 10. Prime mover 13 may also provide power to other systems and components of machine 10.

Implement system 14 may include one or more linkage members configured to move a load. In one example, the implement system may include a boom member 19, a stick member 20, and a work implement or tool 15 such as a bucket. A first end (not shown) of boom member 19 may be pivotally connected to platform 11 to permit the boom member to pivot or rotate relative to the platform. A second end 22 of boom member 19 may be pivotally connected to a first end 23 of stick member 20 to permit the stick member to pivot or relative to the boom member. A first end 26 of the work implement or tool 15 may be pivotally connected to a second end 25 of stick member 20 to permit the tool to pivot or rotate relative to the stick member. The linkage members may translate or rotate in a plane that is generally orthogonal to the platform 11.

The linkage members may be operatively connected to an actuator system 30 that includes one or more actuators such as hydraulic cylinders. Boom member 19 may be propelled or moved along a path by a pair of boom hydraulic cylinders 31 (only one being shown in FIG. 1). Stick member 20 may be propelled by a stick hydraulic cylinder 32.

Rotation of the tool 15 relative to the stick member 20 may be effected by actuation of the tool hydraulic cylinder 33.

Figure 2:
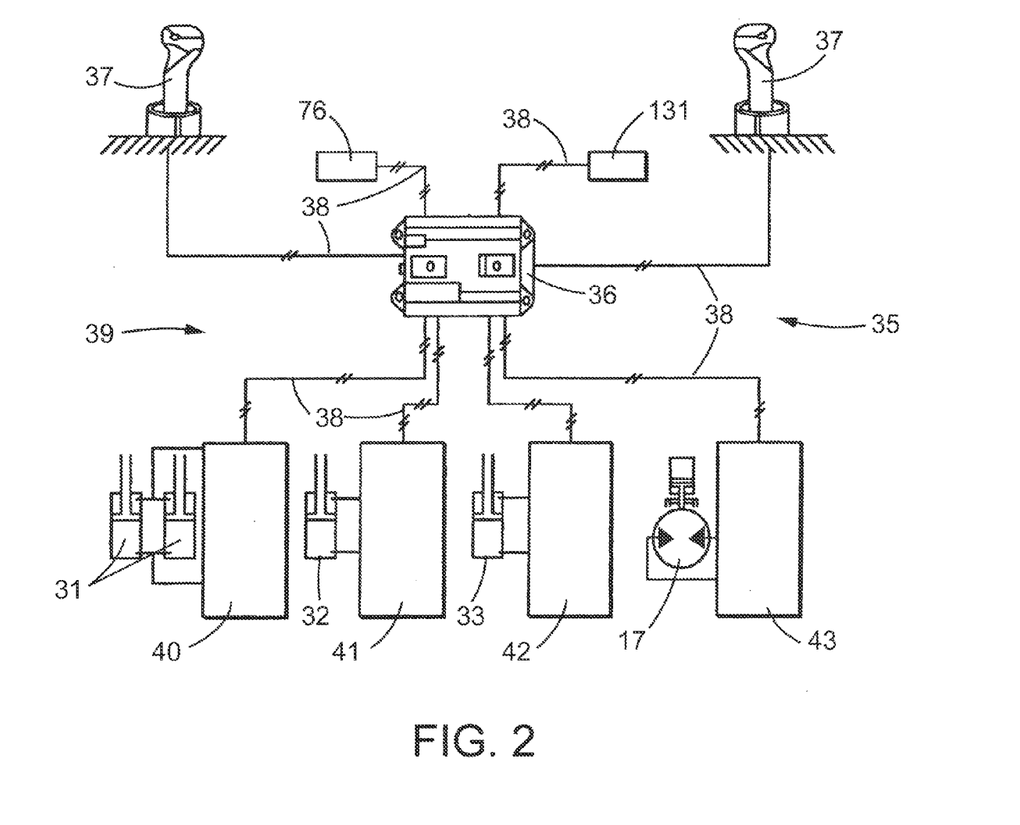
FIG. 2 illustrates a simplified schematic view of a control system of the hydraulic excavator of FIG. 1.

Each of the boom hydraulic cylinders 31, the stick hydraulic cylinder 32, and the tool hydraulic cylinder 33 may embody a linear actuator as depicted in FIG. 2 having a tubular or cylindrical body and a piston and rod assembly therein arranged to form two distinct pressure chambers. The pressure chambers may be selectively supplied with pressurized fluid and drained of the pressurized fluid to cause the piston and rod assembly to displace within the cylindrical body. The flow rate of fluid into and out of the pressure chambers may relate to the speed of extension or retraction of the hydraulic cylinders while a pressure differential between the two pressure chambers may relate to the force imparted by the hydraulic cylinders to their associated linkage members. The extension and retraction of the hydraulic cylinders results in the movement of the linkage members including tool 15. It is also contemplated that the actuators may alternatively embody electric motors, pneumatic motors, or any other actuation devices.

Swing motor 17 may also be driven by differential fluid pressure. Specifically, swing motor 17 may be a rotary actuator including first and second chambers (not shown) located on opposite sides of an impeller (not shown). Upon filling the first chamber with pressurized fluid and draining the second chamber of fluid, the impeller is urged to rotate in a first direction. Conversely, when the first chamber is drained of fluid and the second chamber is filled with pressurized fluid, the impeller is urged to rotate in an opposite direction. The flow rate of fluid into and out of the first and second chambers affects the rotational speed of swing motor 17, while a pressure differential across the impeller affects the output torque thereof.

Machine 10 may be equipped with a plurality of sensors that provide data, directly or indirectly, of the performance or conditions of various aspects of the machine. The term "sensor" is meant to be used in its broadest sense to include one or more sensors and related components that may be associated with the machine 10 and that may cooperate to sense various functions, operations, and operating characteristics of the machine. For example, fuel usage sensor 76 (FIG. 2) may be provided to sense and indicate the amount of fuel being used by the engine. Further, prime mover speed sensor 131 may be provided to sense and indicate the speed of the engine.

Referring to FIG. 2, a control system 35 may be provided to control the operation of the machine 10. The control system 35 may include an electronic control module such as controller 36. The controller 36 may receive operator input commands or signals and control the operation of the various systems of the machine 10. The control system 35 may include one or more operator input devices 37 such as a joystick to control the machine 10 and one or more sensors. The controller 36 may communicate with the sensors, the operator input devices 37, and other components via communication lines 38 or wirelessly.

The controller 36 may be an electronic controller that operates in a logical fashion to perform operations, execute control algorithms, store and retrieve data and other desired operations. The controller 36 may include or access memory, secondary storage devices, processors, and any other components for running an application. The memory and secondary storage devices may be in the form of read-only memory (ROM) or random access memory (RAM) or integrated circuitry that is accessible by the controller. Various other circuits may be associated with the controller such as power supply circuitry, signal conditioning circuitry, driver circuitry, and other types of circuitry.

The controller 36 may be a single controller or may include more than one controller disposed to control various functions and/or features of the machine 10. The term "controller" is meant to be used in its broadest sense to include one or more controllers and/or microprocessors that may be associated with the machine 10 and that may cooperate in controlling various functions and operations of the machine. The functionality of the controller 36 may be implemented in hardware and/or software without regard to the functionality. The controller 36 may rely on one or more data maps relating to the operating conditions of the machine 10 that may be stored in the memory of controller. Each of these maps may include a collection of data in the form of tables, graphs, and/or equations. The controller 36 may use the data maps to maximize the performance and efficiency of the machine 10.

The boom hydraulic cylinders 31, the stick hydraulic cylinder 32, the tool hydraulic cylinder 33, and the swing motor 17 may function together with other cooperating fluid components to move tool 15 in response to input received from the operator input device 37. In particular, control system 35 may include one or more fluid circuits (not shown) configured to produce and distribute streams of pressurized fluid. One or more boom control valves 40, one or more stick control valves 41, one or more tool control valves 42, and one or more swing control valves 43 may be configured or positioned to receive the streams of pressurized fluid and selectively meter the fluid to and from the boom hydraulic cylinders 31, the stick hydraulic cylinder 32, the tool hydraulic cylinder 33, and the swing motor 17, respectively, to regulate the motions thereof.

Controller 36 may be configured to receive input from the operator input device 37 and to command operation of the boom control valves 40, the stick control valves 41, the tool control valves 42, and the swing control valves 43 in response to the input and based on the data maps described above. More specifically, controller 36 may receive an input device position signal indicative of a desired speed and/or type of movement in a particular direction and refer to the data maps stored in the memory of controller 36 to determine flow rate values and/or associated positions for each of the supply and drain elements within the boom control valves 40, the stick control valves 41, the tool control valves 42, and the swing control valves 43. The flow rates or positions may then be commanded of the appropriate supply and drain elements to cause filling and/or draining of the chambers of the actuators at rates that result in the desired movement of tool 15.

FIG. 3 depicts a hydraulic power system 39 for providing pressurized hydraulic fluid to operate the various systems within the machine 10. Prime mover 13 such as a combustion engine and/or a non-combustion source of power may be operatively connected to a gear set 45 that is operatively connected to drive one or more pumps such as a first variable displacement hydraulic pump 46, a second variable displacement hydraulic pump 47, and a fan pump 48. A charge pump 49 may be operatively connected to one of the variable displacement hydraulic pumps or may be directly connected to the gear set 45. As depicted in FIG. 3, the charge pump 49 is operatively connected to the first variable displacement hydraulic pump 46.

Each of the variable displacement hydraulic pumps may be configured to discharge high pressure hydraulic fluid with the first variable displacement hydraulic pump 46 being connected to a first output line 50 and the second variable displacement hydraulic pump 47 being connected to a second output line 51. High pressure hydraulic fluid from the first output line 50 and the second output line 51 may be used for any desired purpose such as operating the hydraulic cylinders of the actuator system 30 and the swing motor 17 to move the work implement as well as operating a hydraulic propulsion system to move the machine 10 about the dig site 100.

A first pressure sensor 55 may be operatively associated with the first variable displacement hydraulic pump 46 to monitor the output pressure of the hydraulic fluid exiting from the first hydraulic pump. A first displacement sensor 56 may be operatively associated with the first variable displacement hydraulic pump 46 to monitor the displacement of the first hydraulic pump. A second pressure sensor 57 may be operatively associated with the second variable displacement hydraulic pump 47 to monitor the output pressure of the hydraulic fluid exiting from the second hydraulic pump. A second displacement sensor 58 may be operatively associated with the second variable displacement hydraulic pump 47 to monitor the displacement of the second hydraulic pump. Each of the first pressure sensor 55, the first displacement sensor 56, the second pressure sensor 57, and the second displacement sensor 58 may also include a status sensor 59 associated therewith that function to determine whether the pressure and displacement sensors are operating properly.

The status sensors 59 may operate by monitoring the operating status of each of the pressure sensors and the displacement sensors. The status sensors 59 may take any form and thus may be implemented in hardware and/or software. For example, each of the pressure and displacement sensors may include discrete status sensors or the status sensors may be integrally formed as part of the pressure and displacement sensors as depicted in FIG. 3. In another example, the status sensors 59 may be a part of the control system 35 or controller 36 and operate by monitoring the types, frequency or intervals, and range or amplitude of signals from the pressure and displacement sensors. In still another example, the status sensors 59 may form a portion of a calibration and/or diagnostics system of each pressure and displacement sensor. If the signals from the pressure and displacement sensors are outside of desired or expected ranges, the controller 36 may determine that the respective pressure or displacement sensor is not operating properly.

If the status sensors 59 are discrete elements, they may generate status signals that transmitted to and received by controller 36. For example, a first pressure status sensor associated with the first pressure sensor 55 may be configured to generate first pressure sensor status signals indicative of the status of the first pressure sensor. A first displacement status sensor associated with the first displacement sensor 56 may be configured to generate first displacement sensor status signals indicative of the status of the first displacement sensor. A second pressure status sensor associated with the second pressure sensor 57 may be configured to generate second pressure sensor status signals indicative of the status of the second pressure sensor. A second displacement status sensor associated with the second displacement sensor 58 may be configured to generate second displacement sensor status signals indicative of the status of the second displacement sensor.

If the status sensors 59 are not discrete elements, the controller 36 may not receive specific signals but may generate within the controller 36 signals indicative of the status of the sensors. The systems described herein are equally applicable regardless of the manner in which the status signals are generated and/or received by the controller 36.

Fan pump 48 may be a variable displacement pump configured to discharge pressurized hydraulic fluid to a fixed displacement fan pump that is operatively connected to a fan 52. A fan pump pressure sensor 130 may be operatively associated with the fan pump 48 to monitor the output pressure of the hydraulic fluid exiting from the fan pump.

Charge pump 49 may be a fixed displacement pump configured to discharge relatively low pressure hydraulic fluid to a charge pump line 53. The relatively low pressure hydraulic fluid passing through the charge pump line 53 may be used for any desired purpose such as operating control valves (e.g., boom control valves 40, stick control valves 41, tool control valves 42, and swing control valves 43) used to control the position of the actuator system 30.

Hydraulic power system 39 may include speed sensors to monitor the speed and angular acceleration of certain components. For example, a prime mover speed sensor 131 (or engine speed sensor) may be operatively associated or connected to the prime mover 13 and operative to determine an output speed and an angular acceleration of the prime mover. A fan speed sensor 132 may be operatively associated or connected to the fan motor 52 and operative to determine an output speed and an angular acceleration of the fan motor.

Control system 35 and hydraulic power system 39 may be configured as a closed-loop system in which feedback and proper operation of all of the sensors may be required for full operation of all systems associated with machine 10. Absent all of the necessary inputs, the control system 35 may "de-stroke" or reduce the displacement of the pump associated with the failed sensor and the hydraulic power system 39 will operate in a limited or minimum flow condition. In such case, the machine 10 may be substantially inoperative.

In case of a failure of one of the output sensors associated with the first variable displacement hydraulic pump 46 or the second variable displacement hydraulic pump 47 (i.e., first pressure sensor 55, first displacement sensor 56, second pressure sensor 57, or second displacement sensor 58), the control system 35 may include a sensor output estimation system 60 to estimate the output from the variable displacement hydraulic pump associated with the failure. The sensor output estimation system 60 may operate generally by determining an input into the pumps, determining the known outputs from the pumps, and estimating the missing output based upon the input into the pumps and the known outputs.

Figure 4:
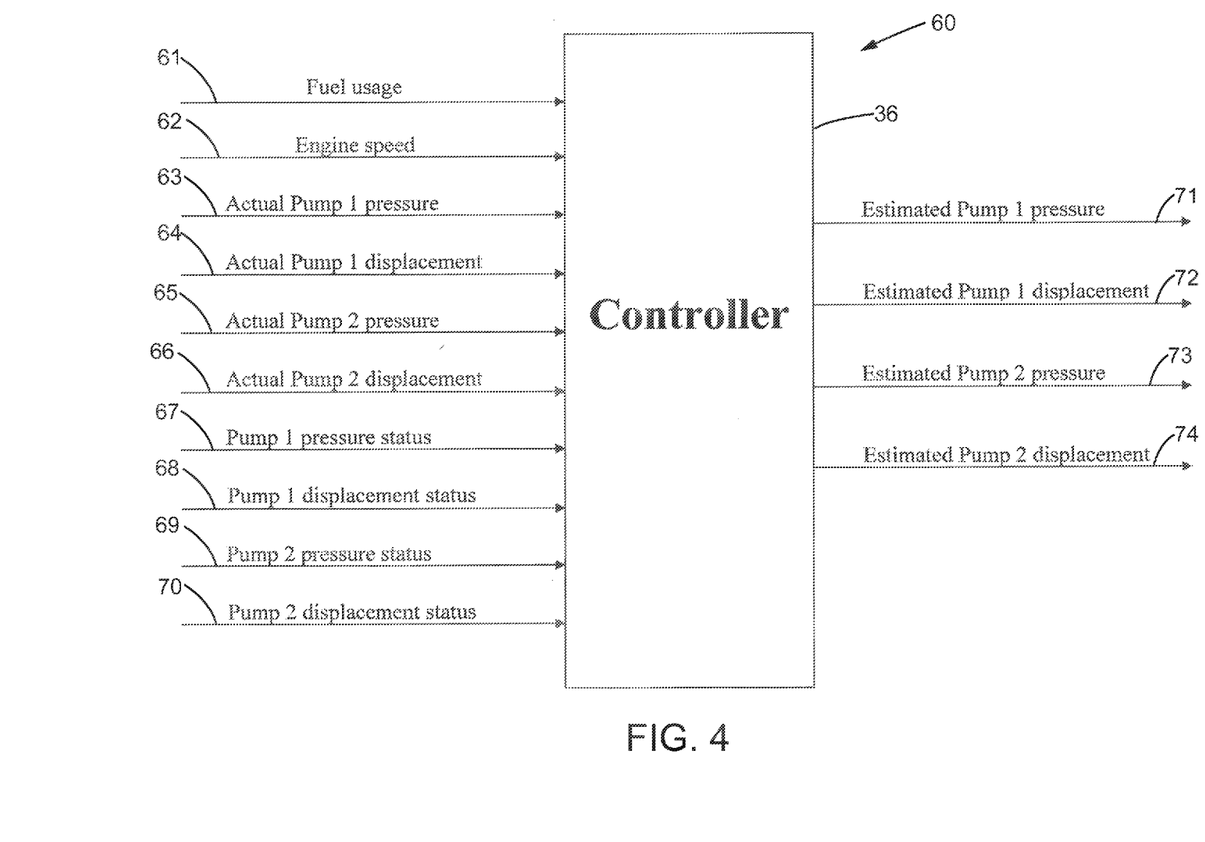
FIG. 4 illustrates a block diagram of a sensor output estimation system of the hydraulic excavator of FIG. 1 depicting all possible inputs and outputs.

As depicted in FIG. 4, the sensor output estimation system 60 may be configured so that the controller 36 receives information from various sensors and systems of the machine 10 and processes the information to generate the necessary or desired estimate from the inoperative sensor. As such, all possible inputs and outputs are depicted in FIG. 4. At node 61, the controller 36 may receive fuel usage signals or data from fuel usage sensor 76 (FIG. 2) indicative of the amount of fuel being used by the prime mover 13. At node 62, the controller 36 may receive engine speed signals or data from prime mover speed sensor 131 (FIG. 2) indicative of the speed of the engine. The controller 36 may use the amount of fuel being used by the prime mover 13 together with the engine speed to determine the output torque from the prime mover. Such determination may be made through the use of look-up tables, data maps, equations, or other aspects of the controller 36.

The combination of the fuel usage sensor 76 and the prime mover speed sensor 131 may act as an equivalent of a torque sensor for generating torque signals indicative of an output torque from the prime mover 13. Other manners of determining the output torque from the prime mover 13 are contemplated. For example, other sensors may be used when using a non-combustion power source.

At node 63, the controller 36 may receive pressure signals or data from the first pressure sensor 55 indicative of the pressure of the hydraulic fluid exiting from the first variable displacement hydraulic pump 46 through first output line 50. At node 64, the controller 36 may receive displacement signals or data from the first displacement sensor 56 indicative of the displacement of the first variable displacement hydraulic pump 46.

At node 65, the controller 36 may receive pressure signals or data from the second pressure sensor 57 indicative of the pressure of the hydraulic fluid exiting from the second variable displacement hydraulic pump 47 through second output line 51. At node 66, the controller 36 may receive displacement signals or data from the second displacement sensor 58 indicative of the displacement of the second variable displacement hydraulic pump 47.

At node 67, controller 36 may receive status signals from the status sensor 59 associated with the first pressure sensor 55 indicative of whether the first pressure sensor is operating properly. At node 68, controller 36 may receive status signals from the status sensor 59 associated with the first displacement sensor 56 indicative of whether the first displacement sensor is operating properly. At node 69, controller 36 may receive status signals from the status sensor 59 associated with the second pressure sensor 57 indicative of whether the second pressure sensor is operating properly. At node 70, controller 36 may receive status signals from the status sensor 59 associated with the second displacement sensor 58 indicative of whether the second displacement sensors operating properly.

Controller 36 may generate an estimate of the output from the sensor that is inoperative. Accordingly, at node 71, in case of a failure of the first pressure sensor 55, the controller 36 may generate signals that are an estimate of the pressure of the hydraulic fluid exiting from the first variable displacement hydraulic pump 46 through first output line 50. At node 72, in case of a failure of the first displacement sensor 56, the controller 36 may generate signals that are an estimate of the displacement of the first variable displacement hydraulic pump 46. At node 73, in case of a failure of the second pressure sensor 57, the controller 36 may generate signals that are an estimate of the pressure of the hydraulic fluid exiting from the second variable displacement hydraulic pump 47 through second output line 51. At node 74, in case of a failure of the second displacement sensor 58, the controller 36 may generate signals that are an estimate of the displacement of the second variable displacement hydraulic pump 47.

Although FIG. 4 depicts an input from each of first pressure sensor 55 (node 63), first displacement sensor 56 (node 64), second pressure sensor 57 (node 65), and second displacement sensor 58 (node 66) and an estimated output from each of those sensors (nodes 71-74), it should be noted that the sensor output estimation system 60 is configured to operate when only one of the sensors is inoperative. The controller 36 thus determines which data is missing and generates an estimate of the missing output. In other words, if all of the pressure sensors and displacement sensors are operating properly, the sensor output estimation system 60 is not necessary and the machine 10 may be operated in its desired manner. However, when only one of the pressure or displacement sensors is not operating properly, the sensor output estimation system 60 is operative to determine an estimate of the missing output signal. Estimates of the output from the sensors that are operating properly will not be generated. The estimated output of the failed sensor may then be used by the control system 35 so that the hydraulic power system 39 is fully operational.

Figure 5:
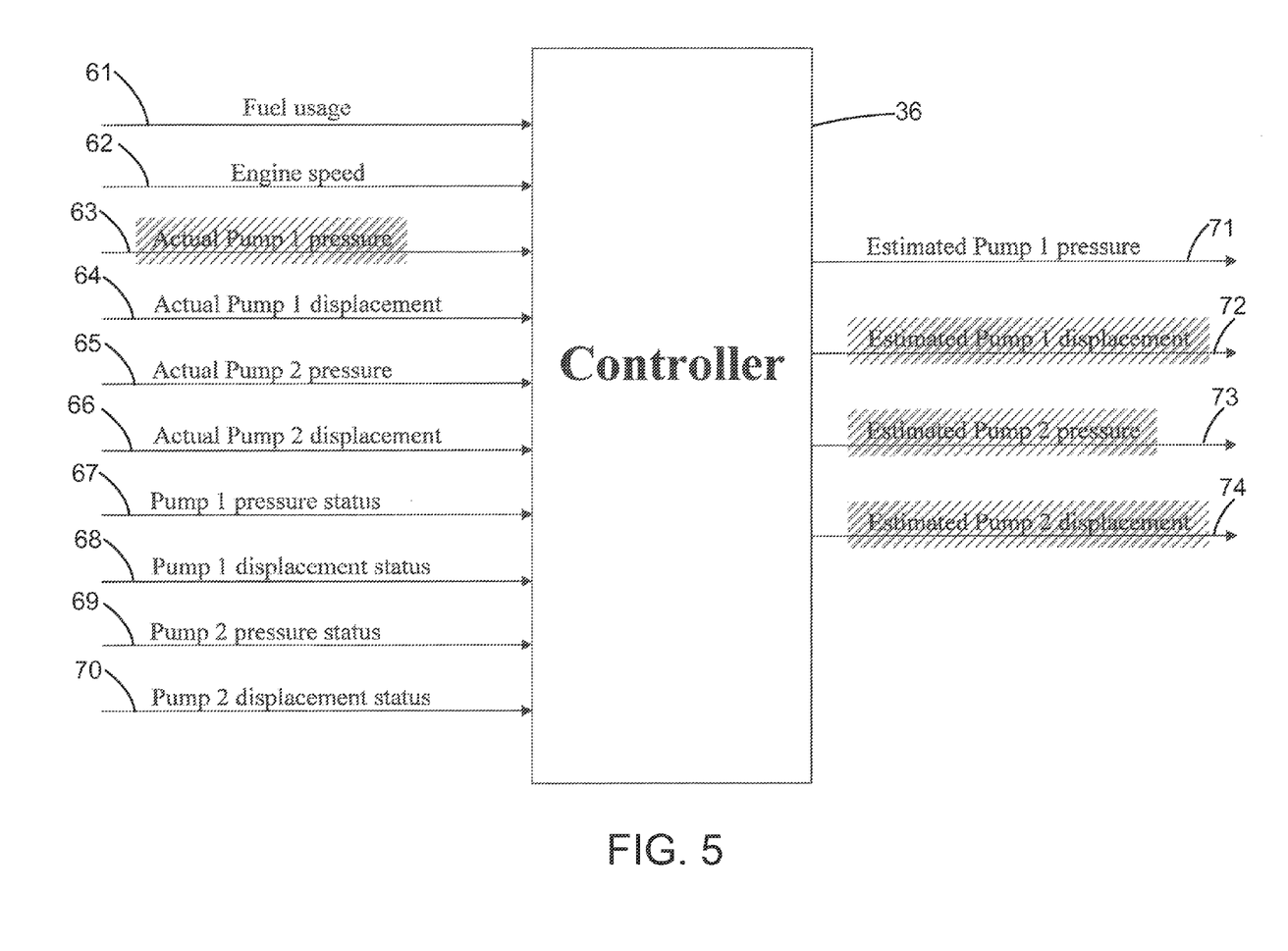
FIG. 5 illustrates the block diagram of FIG. 4 with one pump input sensor inoperable.

Referring to FIG. 5, a second block diagram of the sensor output estimation system 60 is depicted. The block diagram of FIG. 5 is identical to that of FIG. 4 except that it depicts an example in which the first pressure sensor 55 is not operating properly and thus the controller 36 is not receiving input signals or data from the first pressure sensor 55 at node 63. The absence of such input is depicted by striking out the text at node 63. Since the inoperative sensor is the first pressure sensor 55, only an estimate of the output pressure from the first variable displacement hydraulic pump 46 will be generated at node 71. Estimates of the output from the first displacement sensor 56, the second pressure sensor 57, and the second displacement sensor 58 will not be generated. The absence of estimates of the outputs from those sensors is depicted by striking out the text at nodes 72-74.

If the first displacement sensor 56 were inoperative rather than the first pressure sensor 55, the input at node 64 would be omitted and the output at nodes 71 and 73-74 would be omitted. Similarly, an inoperative second pressure sensor 57 would result in an omitted input at node 65 and omitted output at nodes 71-72 and 74 while an inoperative second displacement sensor 58 would result in an omitted input at node 66 and omitted output at nodes 71-73.

Figure 6:
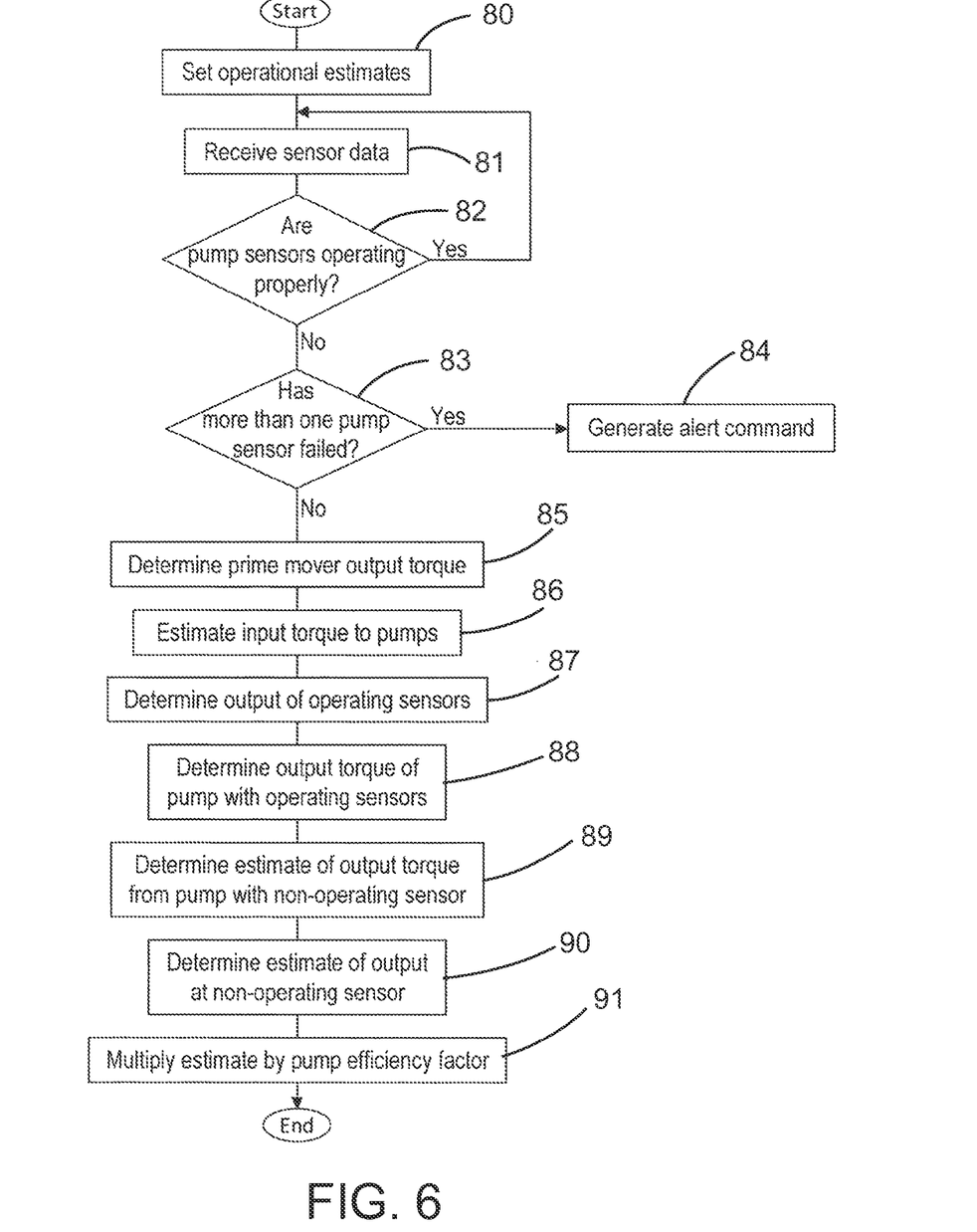
FIG. 6 illustrates a flowchart of the sensor output estimation process in accordance with the disclosure.

A flowchart of the operation of the sensor output estimation system 60 is depicted in FIG. 6. At stage 80, operational estimates and other desired factors utilized to improve the accuracy of the sensor output estimation system 60 may be set or entered within controller 36. For example, an estimate of the amount of energy or torque lost or used to drive the fan pump 48 (and thus fan 52) as well as the charge pump 49 may be set within controller 36. In addition, a pump efficiency factor may also be set or entered within controller 36. The values may be entered by a machine operator, management personnel, technicians, other personnel, or preset at a default value.

At stage 81, the controller 36 may receive data or signals from the various sensors of the machine 10. At decision stage 82, the controller 36 may determine whether the pump sensors are operating properly. To do so, the controller 36 may analyze the signals from the pressure and displacement sensors or from the status sensor 59 associated with each of first pressure sensor 55, first displacement sensor 56, second pressure sensor 57, and second displacement sensor 58. If all of the pump sensors are operating properly at decision stage 82, the controller 36 may continue to receive sensor data at stage 81.

If any of the pump sensors are not operating properly at decision stage 82, the controller 36 may determine at decision stage 83 whether more than one pump sensor has failed. If more than one pump sensor has failed, the controller 36 may generate an alert command at stage 84. The alert command may be operative to notify the machine operator, management personnel, and/or any other desired person or system of the pump sensor failures.

If only one pump sensor has failed, the controller 36 may determine the prime mover output torque at stage 85. In one example, the controller may determine the prime mover output torque based upon the fuel usage and engine speed of the prime mover. In other instances, other manners of determining the prime mover output torque may be utilized. When using a non-combustion source of power, other sensors may be used to determine the prime mover output torque. The controller 36 may determine at stage 86 an estimate of the input torque or input pump torque based upon the prime mover output torque and estimates of fan pump loss and charge pump loss as set at stage 80. In doing so, the controller 36 may subtract estimates of the fan pump loss and charge pump loss from the prime mover output torque.

At stage 87, the controller 36 may determine the output at each of the operating sensors. More specifically, the controller 36 may determine the output pressures from the first variable displacement hydraulic pump 46 and the second variable displacement hydraulic pump 47 based upon data from the first pressure sensor 55 and the second pressure sensor 57, respectively, to the extent that they are operative. Further, the controller 36 may determine the displacements of the first variable displacement hydraulic pump 46 and the second variable displacement hydraulic pump 47 based upon data from the first displacement sensor 56 and the second displacement sensor 58, respectively, to the extent that they are operative.

The controller 36 may determine at stage 88 the output torque of the pump in which both the pressure sensor and the displacement sensor are operative. For example, if one of the second sensors (i.e., second pressure sensor 57 or second displacement sensor 58) is inoperative, the controller 36 may determine at stage 88 the output torque of the first variable displacement hydraulic pump 46. If one of the first sensors (i.e., first pressure sensor 55 or first displacement sensor 56) is inoperative, the controller 36 may determine at stage 88 the output torque of the second variable displacement hydraulic pump 47. To determine the output torque of one of the pumps, the controller 36 may multiply the pressure of the output as determined by the operative pressure sensor by the displacement as determined by the operative displacement sensor.

At stage 89, the controller 36 may determine an estimate of the output torque of the pump having the non-operating sensor. To do so, the controller 36 may subtract the output torque of the pump having the operating sensors calculated at stage 88 from the estimate of the input pump torque determined at stage 86. The remaining torque is approximately equal to the output torque of the pump having the non-operating or inoperative sensor.

At stage 90, the controller 36 may determine an estimate of the output at the non-operating sensor. To do so, the controller 36 may divide the output torque of the pump having the non-operating sensor (as determined at stage 89) by the output of the operating sensor associated with that same pump. In other words, if the pressure sensor of a pump is inoperative, the controller 36 may divide the output torque of that pump by the displacement as determined by the displacement sensor associated with that pump to determine an estimate of the output pressure from the pump. Similarly, if the displacement sensor of a pump is inoperative, the controller 36 may divide the output torque of that pump by the pressure as determined by the pressure sensor associated with that pump to determine an estimate of the displacement of the pump.

If desired, the estimate of the pressure or displacement as determined at stage 90 may be multiplied at stage 91 by the pump efficiency factor set at stage 80. The estimated output from the inoperative sensor may then be used by the controller 36 as input to the control system 35 and hydraulic power system 39 so that the systems and machine 10 remain operative.

If desired, the pump efficiency factor set at stage 80 may be adjusted during operation of the machine 10 prior to a pump sensor failure. To do so, upon determining that the pump sensors are operating properly at decision stage 82, the controller 36 may calculate estimated outputs from each of the pressure sensors and displacement sensors and compare them to the actual outputs from the sensors. To the extent that the estimated outputs are different, the pump efficiency factor may be adjusted so that the estimated outputs more closely match the actual outputs.

Additional or dynamic factors or losses that impact that hydraulic power system 39 may be analyzed, if desired, when generating a model for estimating the output from an inoperative sensor may be generated, if desired, by analyzing. For example, referring to FIG. 3, a torque balance equation for the hydraulic power system 39 may be written as:

$$T_{in} - T_{pump\ 1} - T_{pump\ 2} - T_{gear,ch} - T_{gear,msh} - T_{rotate} - T_{charge} - T_{fan} - T_{inertia} = 0 \quad (1)$$

where $T_{in}$ is the input torque into the hydraulic power system 39 from the prime mover 13;
where $T_{pump\ 1}$ is the output torque of the first variable displacement hydraulic pump 46;
where $T_{pump\ 2}$ is the output torque of the second variable displacement hydraulic pump 47;
where $T_{gear,ch}$ is the gear churning torque loss;
where $T_{gear,msh}$ is the gear mesh torque loss;
where $T_{rotate}$ is the rotational torque loss due to rotational drag of rotating elements or components within the system;
where $T_{charge}$ is the output torque of the charge pump 49;
where $T_{fan}$ is the fan torque loss due to operation of the fan 52; and
where $T_{inertia}$ is the inertia torque loss due to changes in inertia of rotating elements or components within the system.

When operating with a system having only a combustion engine as a prime mover 2, the input torque ($T_{in}$) may be expressed as:

$$k_4 T_{eng} \quad (2)$$

where $T_{eng}$ is the output torque of the engine and $k_4$ is an unknown coefficient or constant. As described above, the input torque from an engine may be determined based upon fuel usage from the fuel usage sensor 76 and the engine speed from the prime mover speed sensor 131.

The torque ($T_{pump\ 1}$) from the first variable displacement hydraulic pump 46 may be expressed as:

$$\frac{P_1 D_1}{\eta_1} \quad (3)$$

where $P_1$ is the discharge pressure from the first variable displacement hydraulic pump 46, $D_1$ is the displacement of the first variable displacement hydraulic pump, and $\eta_1$ is the pump efficiency factor of the first variable displacement hydraulic pump. The torque ($T_{pump\ 2}$) from the second variable displacement hydraulic pump 47 may be expressed in an identical manner by applying the discharge pressure, the displacement, and the pump efficiency factor of the second variable displacement hydraulic pump.

The gear churning torque loss ($T_{gear,ch}$) is the torque loss due to the resistance caused by the viscosity of fluids within the system as components of the system are moved through the fluids and may be estimated based upon the designs of the pumps, test data, as well as the pump efficiency factors. The gear churning torque loss ($T_{gear,ch}$) may be set or stored within controller 36 by an operator, management personnel, a technician, or any other personnel.

The gear mesh torque loss ($T_{gear,msh}$) is the torque loss due to the mechanical losses caused by the interengagement of gears of the system as they rotate and may be estimated based upon the designs of the pumps, test data, as well as the pump efficiency factors. The gear mesh torque loss ($T_{gear,msh}$) may be set or stored within controller 36 by an operator, management personnel, a technician, or any other personnel.

The rotational torque loss ($T_{rotate}$) due to rotational drag of rotating elements or components within the system may be expressed as:

$$k_1 \dot\omega_{eng}^2 \quad (4)$$

where $\dot\omega_{eng}$ is the speed of the engine and $k_1$ is an unknown coefficient.

The output torque ($T_{charge}$) of the charge pump 49 may be expressed as:

$$\frac{P_{charge} D_{charge}}{\eta_{charge}} \quad (5)$$

where $P_{charge}$ is the discharge pressure from the charge pump 49, $D_{charge}$ is the displacement of the charge pump, and $\eta_{charge}$ is the pump efficiency factor of the charge pump.

The fan torque loss ($T_{fan}$) due to operation of the fan 52 may be expressed as:

$$k_2 P_{fan} \omega_{fan} \quad (6)$$

where $P_{fan}$ is the pressure to the fan 52, $\omega_{fan}$ is the speed of the fan, and $k_2$ is an unknown coefficient.

The inertia torque loss ($T_{inertia}$) due to changes in inertia of rotating elements or components within the system may be expressed as:

$$k_3 \dot\omega_{eng} \quad (7)$$

where $\dot\omega_{eng}$ is the angular acceleration of the engine and $k_3$ is an unknown coefficient.

Equations (1)-(7) may be combined and expressed as:

$$k_4 T_{eng} - \frac{P_1 D_1}{\eta_1} - \frac{P_2 D_2}{\eta_2} - T_{gear,ch} - T_{gear,msh} - k_1 \omega_{eng}^2 - \frac{P_{charge} D_{charge}}{\eta_{charge}} - k_2 P_{fan} \omega_{fan} - k_3 \dot\omega_{eng} = 0 \quad (8)$$

Solving Equation (8) for the displacement ($D_1$) of the first variable displacement hydraulic pump 46 results in:

$$D_1 = \frac{\eta_1}{P_1}\left(k_4 T_{eng} - \frac{P_2 D_2}{\eta_2} - T_{gear,ch} - T_{gear,msh} - k_1 \omega_{eng}^2 - \frac{P_{charge} D_{charge}}{\eta_{charge}} - k_2 P_{fan} \omega_{fan} - k_3 \dot\omega_{eng}\right) \quad (9)$$

while solving Equation (8) for the discharge pressure ($P_1$) from the first variable displacement hydraulic pump results in:

$$P_1 = \frac{\eta_1}{D_1}\left(k_4 T_{eng} - \frac{P_2 D_2}{\eta_2} - T_{gear,ch} - T_{gear,msh} - k_1 \omega_{eng}^2 - \frac{P_{charge} D_{charge}}{\eta_{charge}} - k_2 P_{fan} \omega_{fan} - k_3 \dot\omega_{eng}\right) \quad (10)$$

Similarly, solving Equation (8) for the displacement ($D_2$) of the second variable displacement hydraulic pump 47 results in:

$$D_2 = \frac{\eta_2}{P_2}\left(k_4 T_{eng} - \frac{P_1 D_1}{\eta_1} - T_{gear,ch} - T_{gear,msh} - \right. \quad (11)$$
$$\left. k_1 \omega_{eng}^2 - \frac{P_{charge} D_{charge}}{\eta_{charge}} - k_2 P_{fan} \omega_{fan} - k_3 \dot\omega_{eng}\right)$$

while solving Equation (8) for the discharge pressure ($P_2$) from the second variable displacement hydraulic pump results in:

$$P_2 = \frac{\eta_2}{D_2}\left(k_4 T_{eng} - \frac{P_2 D_2}{\eta_2} - T_{gear,ch} - T_{gear,msh} - \right. \quad (12)$$
$$\left. k_1 \omega_{eng}^2 - \frac{P_{charge} D_{charge}}{\eta_{charge}} - k_2 P_{fan} \omega_{fan} - k_3 \dot\omega_{eng}\right)$$

The actual values of the coefficients ($k_1$, $k_2$, $k_3$, $k_4$) are dependent on a plurality of system uncertainties including fluid properties, friction, manufacturing and assembly tolerances. Accordingly, the coefficients of Equations (8)-(12) may be expressed as estimations by including a "^" so as to appear as ($\hat{k}_1$, $\hat{k}_2$, $\hat{k}_3$, $\hat{k}_4$). Equation (8) may thus be re-written as:

$$\hat{k}_4 T_{eng} - \frac{P_1 D_1}{\eta_1} - \frac{P_2 D_2}{\eta_2} - T_{gear,ch} - T_{gear,msh} - \quad (13)$$
$$\hat{k}_1 \omega_{eng}^2 - \frac{P_{charge} D_{charge}}{\eta_{charge}} - \hat{k}_2 P_{fan} \omega_{fan} - \hat{k}_3 \dot\omega_{eng} = 0$$

In addition, Equation (9) may be re-written as:

$$D_1 = \frac{\eta_1}{P_1}\left(\hat{k}_4 T_{eng} - \frac{P_2 D_2}{\eta_2} - T_{gear,ch} - T_{gear,msh} - \right. \quad (14)$$
$$\left. \hat{k}_1 \omega_{eng}^2 - \frac{P_{charge} D_{charge}}{\eta_{charge}} - \hat{k}_2 P_{fan} \omega_{fan} - k_3 \dot\omega_{eng}\right)$$

and Equation (10) may be re-written as:

$$P_1 = \frac{\eta_1}{D_1}\left(\hat{k}_4 T_{eng} - \frac{P_2 D_2}{\eta_2} - T_{gear,ch} - T_{gear,msh} - \right. \quad (15)$$
$$\left. \hat{k}_1 \omega_{eng}^2 - \frac{P_{charge} D_{charge}}{\eta_{charge}} - \hat{k}_2 P_{fan} \omega_{fan} - k_3 \dot\omega_{eng}\right)$$

Equation (11) may be re-written as:

$$D_2 = \frac{\eta_2}{P_2}\left(\hat{k}_4 T_{eng} - \frac{P_2 D_2}{\eta_2} - T_{gear,ch} - T_{gear,msh} - \right. \quad (16)$$
$$\left. \hat{k}_1 \omega_{eng}^2 - \frac{P_{charge} D_{charge}}{\eta_{charge}} - \hat{k}_2 P_{fan} \omega_{fan} - k_3 \dot\omega_{eng}\right)$$

and Equation (12) may be re-written as:

$$P_2 = \frac{\eta_2}{D_2}\left(\hat{k}_4 T_{eng} - \frac{P_2 D_2}{\eta_2} - T_{gear,ch} - T_{gear,msh} - \right. \quad (17)$$
$$\left. \hat{k}_1 \omega_{eng}^2 - \frac{P_{charge} D_{charge}}{\eta_{charge}} - \hat{k}_2 P_{fan} \omega_{fan} - \hat{k}_3 \dot\omega_{eng}\right)$$

In order to estimate the values of the coefficients ($\hat{k}_1$, $\hat{k}_2$, $\hat{k}_3$, $\hat{k}_4$), the controller 36 may utilize a learning process while the first pressure sensor 55, first displacement sensor 56, second pressure sensor 57, and second displacement sensor 58 are all operating properly. More specifically, upon determining that the pump sensors are operating properly at decision stage 82 of FIG. 6, the controller 36 may utilize any desired process to generate estimates of the coefficients ($\hat{k}_1$, $\hat{k}_2$, $\hat{k}_3$, $\hat{k}_4$), use the estimates of the coefficients to calculate the value of one or more terms within the torque balance equation (e.g., Equation (13)), and compare the calculated values to actual or measured values as determined by sensors on the machine 10 or as determined in some other manner. The estimates of the coefficients ($\hat{k}_1$, $\hat{k}_2$, $\hat{k}_3$, $\hat{k}_4$) may be modified until the calculated value and the measured value of the specified terms are sufficiently close or within a desired threshold. Once the calculated value and the measured value of the specified terms are within the desired threshold, the estimated values of the coefficients ($\hat{k}_1$, $\hat{k}_2$, $\hat{k}_3$, $\hat{k}_4$) may be saved within the controller 36 for future use in case of a failure of one of the first pressure sensor 55, the first displacement sensor 56, the second pressure sensor 57, and the second displacement sensor 58.

Figure 7:
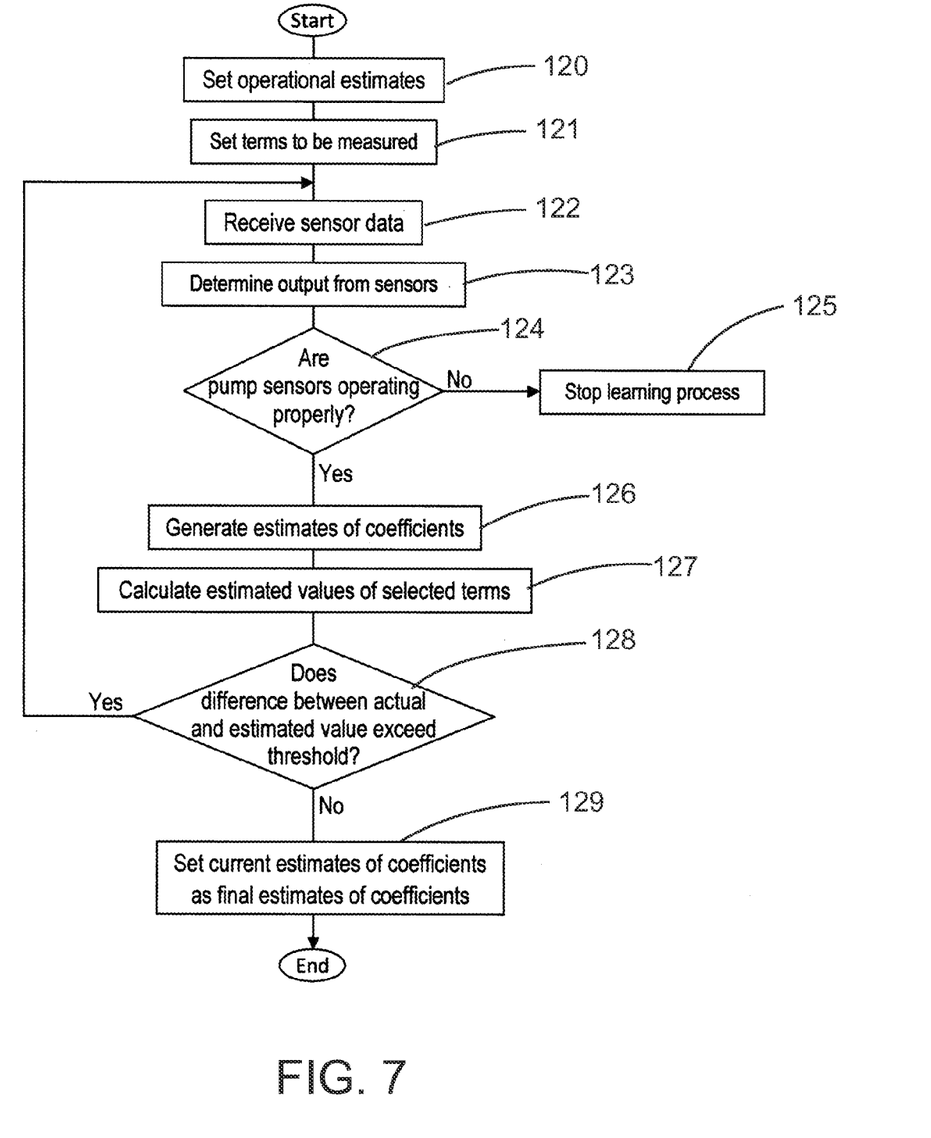
FIG. 7 illustrates a flowchart of the learning process for coefficient estimation in accordance with the disclosure.

Referring to FIG. 7, a flowchart of a learning process within the controller 36 for coefficient estimation is depicted. At stage 120, operational estimates such as gear churning torque loss ($T_{gear,ch}$) and the gear mesh torque loss ($T_{gear,msh}$) may be set or stored within controller 36. At stage 121, one or more terms in Equation (13) that may actually be measured are set or selected for use in determining the estimates of the coefficients ($\hat{k}_1$, $\hat{k}_2$, $\hat{k}_3$, $\hat{k}_4$). For example, since the hydraulic power system 39 includes first pressure sensor 55, first displacement sensor 56, second pressure sensor 57, and second displacement sensor 58, any or all of the first displacement ($D_1$) of the first variable displacement pump 46, the first discharge pressure ($P_1$) from the first variable displacement pump, the second displacement ($D_2$) of the second variable displacement pump 47, the second discharge pressure ($P_2$) from the second variable displacement pump may be used to generate estimates of the coefficients ($\hat{k}_1$, $\hat{k}_2$, $\hat{k}_3$, $\hat{k}_4$).

For each term from Equation (13) that has been selected for use as part of the coefficient estimation process, Equation (13) may be re-written to solve for that term. For example, if the first discharge pressure ($D_1$) from the first variable displacement pump 46 and the second discharge pressure ($D_2$) from the second variable displacement pump 47 are set as the terms to be measured, Equations (13) may be re-written as set forth in Equations (14) and (16), respectively.

At stage 122, the controller 36 may receive data or signals from the various sensors of the machine 10. At stage 123, the controller 36 may determine the output from each of the sensors. The output from the sensors may include the terms in Equation (13) that have been selected for use in generating the estimates of the coefficients ($\hat{k}_1$, $\hat{k}_2$, $\hat{k}_3$, $\hat{k}_4$).

At decision stage 124, the controller 36 may determine whether each of the pump sensors is operating properly. If the pump sensors are not operating properly, the controller 36 may stop the coefficient estimation process at stage 125. If the pump sensors are operating properly, the controller 36 may generate at stage 126 initial estimates of the coefficients ($\hat{k}_1$, $\hat{k}_2$, $\hat{k}_3$, $\hat{k}_4$). Based upon the initial estimates of the coefficients ($\hat{k}_1$, $\hat{k}_2$, $\hat{k}_3$, $\hat{k}_4$), the controller 36 may solve at stage 127 the re-written forms of Equation (13) (such as Equations (14) and (16)) to generate estimated values for the selected terms.

At stage 128, the controller 36 may compare the actual value of the selected terms to the value of those terms calculated based upon the estimates of the coefficients ($\hat{k}_1$, $\hat{k}_2$, $\hat{k}_3$, $\hat{k}_4$). If the difference between the actual values and the estimated values is less than a predetermined threshold, the controller 36 may at stage 129 set the final estimated values of the coefficients ($\hat{k}_1$, $\hat{k}_2$, $\hat{k}_3$, $\hat{k}_4$) as those set at stage 125. If the difference between the actual values and the estimated values is less than a predetermined threshold, the controller 36 may repeat the process beginning at stage 122 including generating new estimated values of the coefficients ($\hat{k}_1$, $\hat{k}_2$, $\hat{k}_3$, $\hat{k}_4$).

Any desired process may be used to generate estimates of the coefficients ($\hat{k}_1$, $\hat{k}_2$, $\hat{k}_3$, $\hat{k}_4$). In one example, the controller 36 may utilize an adaptive learning process or rule such as a negative gradient method to determine or generate estimates of the coefficients. In doing so, the process will permit the controller 36 to select subsequent estimates of the coefficients ($\hat{k}_1$, $\hat{k}_2$, $\hat{k}_3$, $\hat{k}_4$) to reduce the difference between the actual value of the selected terms and the calculated value of those terms. In another example, the controller 36 may utilize an intensive computational method as an adaptive learning process to generate estimates of the coefficients ($\hat{k}_1$, $\hat{k}_2$, $\hat{k}_3$, $\hat{k}_4$). Additional methods of determining estimates of the coefficients are contemplated.

Once the final estimates of the coefficients ($\hat{k}_1$, $\hat{k}_2$, $\hat{k}_3$, $\hat{k}_4$) have been set at stage 129, any of Equations (14)-(17) may be used to determine the output in case of a failure of one of the first pressure sensor 55, the first displacement sensor 56, the second pressure sensor 57, and the second displacement sensor 58. Since the input torque ($T_{in}$) into the hydraulic power system, the rotational torque loss ($T_{rotate}$), the fan torque loss ($T_{fan}$), and the inertia torque loss ($T_{inertia}$) each include one of the are dependent on the estimates of the coefficients ($\hat{k}_1$, $\hat{k}_2$, $\hat{k}_3$, $\hat{k}_4$), the controller 36 may use an adaptive learning process to determine in part the value of each of the relevant terms.

As stated above, the estimates of the coefficients ($\hat{k}_1$, $\hat{k}_2$, $\hat{k}_3$, $\hat{k}_4$) may be determined by comparing an actual output to an estimated output of one or more terms. In some instances, it may be undesirable to determine the estimates of the coefficients ($\hat{k}_1$, $\hat{k}_2$, $\hat{k}_3$, $\hat{k}_4$) based upon more than one term. For example, the hydraulic power system 39 of FIG. 3 includes a first variable displacement hydraulic pump 46 and a second variable displacement hydraulic pump 47. Utilizing only one term (such as the first discharge pressure ($D_1$)) to determine the estimated values of the coefficients ($\hat{k}_1$, $\hat{k}_2$, $\hat{k}_3$, $\hat{k}_4$) may reduce the accuracy of the estimated coefficients since they are not comparing actual and estimated values for both of the pumps. Accordingly, it may be desirable to compare an actual value to an estimated value for at least one term for each pump within a system.

It should be noted that although the torque balance equation set forth as Equation (1) includes a plurality factors for calculating or estimating torque loss, all of the factors may not be necessary to generate a sufficiently accurate estimation of a sensor output for a particular system.

INDUSTRIAL APPLICABILITY

The industrial applicability of the sensor output estimation system 60 described herein will be readily appreciated from the foregoing discussion. The present disclosure is applicable to machines 10 having one or more variable displacement hydraulic pumps. One exemplary machine for which the sensor output estimation system 60 is suited is an excavator or hydraulic shovel. However, the sensor output estimation system 60 may be applicable to other machines in which an approximation of an output value from a variable displacement hydraulic pump is desirable when an exact value is not available such as due to a sensor failure.

The disclosed sensor output estimation system 60 provides many advantages while operating a machine. In case of a failure of one of the output sensors associated with a variable displacement hydraulic pump, the controller 36 may be configured to determine an approximate value of the output associated with the inoperative sensor and thus permit the control system 35 and the hydraulic power system 39 to remain fully or close to fully operational. This permits an operator to continue to operate machine 10 in a productive manner even while waiting for replacement of the inoperative sensor.

It will be appreciated that the foregoing description provides examples of the disclosed system and technique. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

The invention claimed is:
1. A system for determining an estimated output from a variable displacement hydraulic pump, comprising:
   a variable displacement hydraulic pump;
   a prime mover operatively connected to drive the variable displacement hydraulic pump;
   a torque sensor for generating torque signals indicative of an output torque from the prime mover;
   a pressure sensor for generating pressure signals indicative of an output pressure from the variable displacement hydraulic pump;
   a displacement sensor for generating displacement signals indicative of a displacement of the variable displacement hydraulic pump;
   a prime mover speed sensor operatively associated with the prime mover and operative to determine an angular acceleration of the prime mover;
   and
   a controller configured to:
      receive torque signals from the torque sensor;
      determine the output torque from the prime mover;
      determine an input torque to the variable displacement hydraulic pump based upon the output torque;
      receive signals from one of the pressure sensor and the displacement sensor;

determine an output from the one of the pressure sensor and the displacement sensor based upon the signals;

determine an inertia torque loss based upon the angular acceleration of the prime mover;

determine a failure of another of the pressure sensor and the displacement sensor; and determine an estimated output from the another of the pressure sensor and the displacement sensor based upon the input torque to the variable displacement hydraulic pump, the output from the one of the pressure sensor and the displacement sensor, and the inertia torque loss.

2. The system of claim 1, wherein the prime mover speed sensor is further operative to determine an angular speed of the prime mover and the controller is further configured to determine a rotational torque loss based upon the angular speed and determine the estimated output further based upon the rotational torque loss.

3. The system of claim 2, wherein the controller is further configured to use an adaptive learning process to determine in part the rotational torque loss.

4. The system of claim 1, wherein the controller is further configured to determine the estimated output only upon determining a failure of only one of the pressure sensor and the displacement sensor.

5. The system of claim 1, further including a charge pump operatively connected to the prime mover, and the controller is further configured to determine an output torque from the charge pump based upon an output pressure from the charge pump and the displacement of the charge pump, and determine the estimated output further based upon the charge pump torque.

6. The system of claim 5, wherein the charge pump is operatively connected to the variable displacement hydraulic pump.

7. The system of claim 1, further including a fan operatively connected to the prime mover and a fan speed sensor operative to determine an angular fan speed of the fan, and the controller is further configured to determine a fan torque loss based upon the angular fan speed and determine the estimated output further based upon the fan torque loss.

8. The system of claim 7, further including a fan pump operatively connected to the prime mover and a fan pump pressure sensor operatively associated with the fan pump to determine an output pressure from the fan pump, and the controller is configured to determine the fan torque loss further based upon the output pressure from the fan pump.

9. The system of claim 8, wherein the controller is further configured to use an adaptive learning process to determine in part the fan torque loss.

10. The system of claim 1, further including a second variable displacement hydraulic pump driven by the prime mover;

a second sensor for generating second signals indicative of an output torque from the second variable displacement hydraulic pump; and the controller is further configured to:
receive second signals from the second sensor;
determine the output torque of the second variable displacement hydraulic pump based upon the second signals;
determine the estimated output further based upon the output torque from the second variable displacement hydraulic pump.

11. The system of claim 10, wherein the controller is further configured to determine the estimated output based upon a first pump efficiency factor of the variable displacement hydraulic pump and a second pump efficiency factor of the second variable displacement hydraulic pump.

12. The system of claim 1, further including a second variable displacement hydraulic pump driven by the prime mover;

a second pressure sensor for generating second pressure signals indicative of a second output pressure from the second variable displacement hydraulic pump;

a second displacement sensor for generating second displacement signals indicative of a second displacement of the second variable displacement hydraulic pump; and the controller is further configured to:
receive the second pressure signals from the second pressure sensor;
determine a second output pressure from the second variable displacement hydraulic pump based upon the second pressure signals from the second pressure sensor;
receive the second displacement signals from the second displacement sensor;
determine a second displacement of the second variable displacement hydraulic pump based upon the second displacement signals from the second displacement sensor; and
determine the estimated output further based upon the output from the second pressure sensor and the output from the second displacement sensor.

13. The system of claim 12, wherein the controller is further configured to determine the estimated output only upon determining a failure of only one of the pressure sensor, the displacement sensor, the second pressure sensor, and the second displacement sensor.

14. The system of claim 1, wherein the controller is further configured to use an adaptive learning process to determine in part the input torque to the variable displacement hydraulic pump.

15. The system of claim 1, wherein the controller is further configured to use an adaptive learning process to determine in part the inertia torque loss.

16. The system of claim 1, wherein the controller is further configured to store one of a gear churning torque loss and a gear mesh torque loss and determine the estimated output based upon the one of the gear churning torque loss and the gear mesh torque loss.

17. The system of claim 1, wherein the controller is further configured to store one of a gear churning torque loss and a gear mesh torque loss and determine the estimated output based upon the one of the gear churning torque loss and the gear mesh torque loss.

18. A controller-implemented method of determining an estimated output from a variable displacement hydraulic pump, comprising:

providing a variable displacement hydraulic pump;
providing a pressure sensor for generating pressure signals indicative of an output pressure from the variable displacement hydraulic pump;
providing a displacement sensor for generating displacement signals indicative of a displacement of the variable displacement hydraulic pump;
receiving torque signals from a torque sensor indicative of an output torque from a prime mover;
determining the output torque from the prime mover based upon the torque signals;
determining an input torque to the variable displacement hydraulic pump based upon the output torque;
receiving signals from one of the pressure sensor and the displacement sensor;

determining an output from the one of the pressure sensor and the displacement sensor based upon the signals;

determining an inertia torque loss based upon an angular acceleration of the prime mover;

determining a failure of another of the pressure sensor and the displacement sensor; and determining an estimated output from the another of the pressure sensor and the displacement sensor based upon the input torque to the variable displacement hydraulic pump, the output from the one of the pressure sensor and the displacement sensor, and the inertia torque loss.

19. The method of claim 18, further including determining an angular speed of the prime mover, determining a rotational torque loss based upon the angular speed, and determining the estimated output further based upon the rotational torque loss.

20. A machine comprising:

a variable displacement hydraulic pump;

a prime mover operatively connected to drive the variable displacement hydraulic pump;

a torque sensor for generating signals indicative of an output torque from the prime mover;

a pressure sensor for generating pressure signals indicative of an output pressure from the variable displacement hydraulic pump;

a displacement sensor for generating displacement signals indicative of a displacement of the variable displacement hydraulic pump; and a prime mover speed sensor operatively associated with the prime mover and operative to determine an angular acceleration of the prime mover;

a controller configured to:

receive torque signals from the torque sensor;

determine the output torque from the prime mover;

determine an input torque to the variable displacement hydraulic pump based upon the output torque;

receive signals from one of the pressure sensor and the displacement sensor;

determine an output from the one of the pressure sensor and the displacement sensor based upon the signals;

determine an inertia torque loss based upon the angular acceleration of the prime mover;

determine a failure of another of the pressure sensor and the displacement sensor; and determine an estimated output from the another of the pressure sensor and the displacement sensor based upon the input torque to the variable displacement hydraulic pump, the output from the one of the pressure sensor and the displacement sensor, and the inertia torque loss.

* * * * *